United States Patent
Birkhoff et al.

(10) Patent No.: US 9,212,107 B2
(45) Date of Patent: Dec. 15, 2015

(54) PROCESS FOR PRODUCING CUMENE

(71) Applicant: BADGER LICENSING LLC, Boston, MA (US)

(72) Inventors: Ronald Birkhoff, Houston, TX (US); Shyh-Yuan H. Hwang, Needham, MA (US)

(73) Assignee: BADGER LICENSING LLC, Boston, MA (US)

( * ) Notice: Subject to any disclaimer, the term of this patent is extended or adjusted under 35 U.S.C. 154(b) by 0 days.

(21) Appl. No.: 14/412,275

(22) PCT Filed: Jul. 2, 2013

(86) PCT No.: PCT/US2013/049079
§ 371 (c)(1),
(2) Date: Dec. 31, 2014

(87) PCT Pub. No.: WO2014/008268
PCT Pub. Date: Jan. 9, 2014

(65) Prior Publication Data

US 2015/0158790 A1 Jun. 11, 2015

Related U.S. Application Data

(60) Provisional application No. 61/668,284, filed on Jul. 5, 2012.

(51) Int. Cl.
| | |
|---|---|
| C07C 2/86 | (2006.01) |
| C07C 29/145 | (2006.01) |
| C07C 407/00 | (2006.01) |
| C07C 45/53 | (2006.01) |
| C07C 37/08 | (2006.01) |

(52) U.S. Cl.
CPC .............. *C07C 2/864* (2013.01); *C07C 29/145* (2013.01); *C07C 37/08* (2013.01); *C07C 45/53* (2013.01); *C07C 407/00* (2013.01); *C07C 2529/70* (2013.01)

(58) Field of Classification Search
None
See application file for complete search history.

(56) References Cited

U.S. PATENT DOCUMENTS

| | | | |
|---|---|---|---|
| 5,015,786 A | 5/1991 | Araki et al. | |
| 6,512,153 B1 | 1/2003 | Cappellazzo et al. | |
| 6,841,704 B2 * | 1/2005 | Sakuth et al. ................ | 568/798 |
| 2011/0218366 A1 | 9/2011 | Lorenzoni et al. | |
| 2011/0313213 A1 | 12/2011 | Minoux et al. | |

OTHER PUBLICATIONS

International Search Report and Written Opinion issued in the corresponding PCT/US2013/049079 on Nov. 8, 2013.

\* cited by examiner

*Primary Examiner* — Brian J Davis
(74) *Attorney, Agent, or Firm* — Roberts Mlotkowski Safran & Cole, P.C.

(57) ABSTRACT

In a process for producing cumene, isopropanol containing nitrogenous impurities is reacted with benzene in an alkylation reactor to produce an effluent stream comprising cumene, unreacted benzene and water. Water is removed from the effluent stream and an aliquot of the resultant dried effluent stream is treated to remove nitrogenous impurities and produce a purified recycle stream. At least part of the purified recycle stream is then recycled to the alkylation reactor. In an alternative embodiment, the isopropanol is combined with fresh and/or recycled benzene and the combined stream is treated to remove nitrogenous impurities before being fed to the alkylation reactor.

17 Claims, 3 Drawing Sheets

Prior Art

PROCESS FOR PRODUCING CUMENE

CROSS-REFERENCE TO RELATED APPLICATIONS

The present application is a U.S. National Phase of PCT/US2013/049079 filed on Jul. 2, 2013 claiming priority to U.S. provisional application No. 61/668,284 filed Jul. 5, 2012. The disclosure of the PCT Application is hereby incorporated by reference into the present Application.

FIELD

This invention relates to a process for producing cumene and particularly, but not exclusively, to an integrated process for producing cumene and for converting the cumene to phenol.

BACKGROUND

Cumene is an important intermediate in the chemical and polymer industries, with global cumene production currently exceeding twelve million metric tons annually. The majority of all cumene manufactured in the world today is used for the production of phenol. The demand for phenol for the manufacture of Bisphenol-A and subsequently polycarbonates is accelerating, owing to the broadening applications of polycarbonates in the electronic, healthcare, and automobile industries.

The rapid growth of cumene, phenol and Bisphenol-A production, however, has caused some concerns related to the imbalance of the acetone byproduct produced from the phenol plant. Thus, acetone and phenol are produced at an approximately 1:1 molar ratio from cumene, but are used at an approximately 1:2 molar ratio in the downstream Bisphenol-A production process. The excess acetone that is not used in the production of Bisphenol-A has caused some concern from phenol producers in that it may create a supply-demand imbalance and disrupt the economics of the phenol production business.

In addition, cumene is typically produced by reacting benzene and propylene under liquid phase or mixed gas-liquid phase conditions in the presence of acid catalysts, particularly zeolite catalysts. The resultant need to locate integrated cumene/phenol plants near a source of propylene has become an important issue with producers. Thus, in today's olefins market, there is also a supply-demand imbalance in the supply of propylene produced from conventional sources, such as ethylene plants, due to the availability of feedstocks that favor the production of propylene. This imbalance has forced phenol producers to build their plants closer to feedstock supplies rather than to product outlets.

Numerous research efforts have been directed at solving the acetone imbalance and propylene supply issues described above by recycling the excess acetone produced in the phenol plant to produce cumene. For example, U.S. Pat. No. 5,015,786 teaches a process for preparing phenol, comprising the steps of: (a) alkylating benzene with isopropanol using a zeolite catalyst under liquid phase conditions to synthesize cumene, (b) oxidizing the cumene from step (a) with molecular oxygen into cumene hydroperoxide, (c) subjecting cumene hydroperoxide to acid cleavage to synthesize phenol and acetone, and (d) hydrogenating the acetone from step (c) with hydrogen gas under liquid phase conditions into isopropanol which is recycled to step (a).

One problem involved in manufacturing cumene by the alkylation of benzene with isopropanol over a zeolite catalyst is that one mole of water is produced for every mole of isopropanol consumed during the reaction. Not only does this require the provision of significant downstream treatment facilities to remove water from the product but also most zeolites show decreased selectivity and increased aging in the presence of excessive amounts of water. It is therefore desirable to maintain the water concentration at the outlet of the isopropanol alkylation reactor at about 1 wt %. As disclosed in, for example, U.S. Pat. No. 6,512,153, this is conveniently achieved by controlling the rate of alkylation and recycling part of the reaction effluent after drying to remove the water by-product.

Another problem encountered in using isopropanol produced from the excess acetone from a phenol plant in the production of cumene is that the acetone tends to contain significant quantities of nitrogen impurities which carry over into the isopropanol intermediate product. Such impurities act as poisons to the zeolite catalyst employed in the downstream alkylation step and so must be removed or reduced to very low levels. However, attempts to remove these impurities from the acetone and isopropanol feeds with conventional solid acid adsorbents have proved to be only marginally effective due to the molecular polarity of the acetone and isopropanol, which competes with the adsorption of the polar nitrogen compounds. Also, the high water solubility of acetone and isopropanol eliminates the use of water washing, which is also commonly employed to remove nitrogen compounds from hydrocarbon streams.

In accordance with the present invention, it has now been found that, when isopropanol is produced from acetone and is used in the alkylation of benzene to produce cumene, the deleterious effects of any nitrogen impurities in the isopropanol can be effectively ameliorated by treatment of the dried recycle stream to the alkylation reactor. In addition, by effecting the treatment on the dried recycle stream, the removal of the nitrogen impurities can be achieved by adsorption on acidic solid adsorbents, such as molecular sieves or acidic clay, and/or by treatment with an acidic water solution, such as dilute sulfuric acid. Alternatively, the isopropanol can be mixed with fresh benzene and the resulting mixture treated to remove the nitrogen impurities. In this case, the dilution effect of the benzene on the polarity of the isopropanol is found to be sufficient to allow the use of solid acid adsorbents in the nitrogen removal. Moreover, treatment of the benzene/isopropanol mixture can be used to remove nitrogen and other impurities from the fresh benzene.

SUMMARY

In one aspect, the invention resides in a process for producing cumene, the process comprising:

(a) contacting benzene with a $C_3$ alkylating agent comprising isopropanol, and optionally propylene, under alkylation conditions such that at least part of the $C_3$ alkylating agent reacts with the benzene to produce an alkylation effluent comprising cumene, unreacted benzene and water;

(b) recovering cumene from the alkylation effluent;

(c) removing water from the alkylation effluent to form a dried effluent stream;

(d) treating an aliquot of the dried effluent stream to remove nitrogenous impurities therefrom and produce a purified recycle stream; and (e) recycling at least part of the purified recycle stream to the contacting (a).

In a further aspect, the invention resides in an integrated process for producing phenol, the process comprising:

(a) contacting benzene with a $C_3$ alkylating agent comprising isopropanol, and optionally propylene, under alkylation conditions such that at least part of the $C_3$ alkylating agent reacts with the benzene to produce an alkylation effluent comprising cumene, unreacted benzene and water;

(b) separating cumene from the alkylation effluent;

(c) removing water from the alkylation effluent to produce a dried effluent stream;

(d) treating an aliquot of the dried effluent stream to remove nitrogenous impurities therefrom and produce a purified recycle stream;

(e) recycling at least part of the purified recycle stream to the contacting (a);

(f) oxidizing at least part of the cumene separated in (b) to form cumene hydroperoxide;

(g) cleaving at least part of the cumene hydroperoxide from (f) to form a cleavage product stream containing phenol and acetone;

(h) separating at least part of the acetone from the cleavage product stream;

(i) hydrogenating at least part of the acetone separated in (h) to produce isopropanol; and (j) recycling at least part of the isopropanol produced in (h) to the contacting (a).

In one embodiment, the treating (d) includes passing the aliquot of the dried recycle stream through a solid adsorbent, such as a molecular sieve or an acidic clay. Alternatively, the treating (d) includes washing the aliquot of the dried recycle stream with an acidic water solution.

Conveniently, fresh benzene, recycle benzene, and/or fresh $C_3$ alkylating agent is mixed with the aliquot of the dried recycle steam prior to the treating (d).

In another aspect, the invention resides in a process for producing cumene, the process comprising:

(a) mixing fresh benzene with a $C_3$ alkylating agent comprising isopropanol, and optionally propylene, to produce a combined feed stream;

(b) treating at least part of said combined feed stream to remove nitrogenous impurities therefrom and produce a purified combined feed stream; and (c) contacting said purified combined feed stream with an alkylation catalyst in an alkylation zone under alkylation conditions such that at least part of said isopropanol and benzene react to produce an alkylation effluent comprising cumene.

In yet a further aspect, the invention resides in an integrated process for producing phenol, the process comprising:

(a) mixing fresh benzene with a $C_3$ alkylating agent comprising isopropanol, and optionally propylene, to produce a combined feed stream;

(b) treating at least part of said combined feed stream to remove nitrogenous impurities therefrom and produce a purified combined feed stream;

(c) contacting said purified combined feed stream with an alkylation catalyst in an alkylation zone under alkylation conditions such that the isopropanol reacts with the benzene to produce an alkylation effluent comprising cumene;

(d) recovering cumene from said reaction product;

(e) oxidizing at least part of the cumene recovered in (d) to form cumene hydroperoxide;

(f) cleaving at least part of the cumene hydroperoxide from (e) to form a cleavage product stream containing phenol and acetone;

(g) separating at least part of the acetone from the cleavage product stream;

(h) hydrogenating at least part of the acetone separated in (g) to produce isopropanol; and (i) recycling at least part of the isopropanol produced in (h) to said contacting (a).

DETAILED DESCRIPTION

A process is described for producing cumene by alkylation of benzene with isopropanol in the presence of an acidic catalyst, particularly a molecular sieve catalyst. The source of the isopropanol is not critical but many isopropanol sources contain relatively high levels (up to 10 ppm by weight) of nitrogen impurities which can act as poisons to the alkylation catalyst. The present process provides advantageous methods of reducing the level of these impurities in the feed to the alkylation catalyst so as to enhance the useful life of the catalyst.

In one preferred embodiment, the present process forms part of an integrated process for producing phenol from benzene, in which the cumene produced by the alkylation reaction is oxidized to produce cumene hydroperoxide and the hydroperoxide is then cleaved to produce phenol and acetone. Most of the phenol is routed to the production of Bisphenol-A by reaction with acetone at an approximately 2:1 (phenol to acetone) molar ratio. The excess acetone can then be hydrogenated to produce isopropanol and then recycled to the production of additional cumene by the present process. The ensuing description will therefore focus on this integrated process.

Benzene Alkylation to Produce Cumene

In the first stage of the present process, benzene is alkylated with a $C_3$ alkylating agent comprising isopropanol, optionally together with added propylene, in the presence of a molecular sieve alkylation catalyst. Preferably, the alkylation is conducted under conditions such that at least part of the reaction mixture is maintained in the liquid phase during the process. Typical conditions include a temperature of about 20° C. to about 350° C., for example about 60° C. to about 300° C., a pressure of about 100 kPa to about 20,000 kPa, for example about 500 kPa to about 10,000 kPa, and a molar ratio of benzene to the $C_3$ alkylating agent of about 0.1:1 to about 100:1, such as about 1:1 to about 10:1. Where the $C_3$ alkylating agent contains propylene, the molar ratio of isopropanol to propylene is typically about 1 to 100 to about 100 to 1.

Generally, the alkylation is conducted in the presence hydrogen, either added directly to the alkylation feed or present in the reactor effluent recycled from the acetone hydrogenation stage described below. Thus, it is found that hydrogen assists in removing the water coproduced with cumene in the alkylation step, thereby reducing the contact between the catalyst and the water and hence any tendency for the water to deactivate the catalyst. For some catalysts, the presence of hydrogen during the alkylation stage also reduces deactivation caused by coke formation on the catalyst. Excessive hydrogen should, however, be avoided since it can lead to undesirable loss of benzene to cyclohexane. Conveniently, the molar ratio of hydrogen to isopropanol in said second reaction zone is about 0:1 to about 100:1, such as about 0:1 to about 10:1.

The catalyst employed in the alkylation step may comprise at least one medium pore molecular sieve having a Constraint Index of 2-12 (as defined in U.S. Pat. No. 4,016,218). Suitable medium pore molecular sieves include ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231.

Alternatively, the alkylation catalyst may comprise one or more large pore molecular sieves having a Constraint Index less than 2. Suitable large pore molecular sieves include zeolite beta, zeolite Y, Ultrastable Y (USY), Dealuminized Y (DealY), mordenite, ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Zeolite Beta is described in U.S. Pat. Nos. 3,308,069, and Re. No. 28,341. Low sodium Ultrastable Y molecular sieve (USY) is described in U.S. Pat. Nos. 3,293,192 and 3,449,070. Dealuminized Y zeolite (DealY) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

Preferably, however, the alkylation catalyst comprises at least one molecular sieve of the MCM-22 family. As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Related zeolite UZM-8 is also suitable for use as the present alkylation catalyst.

The above molecular sieves may be used as the alkylation catalyst without any binder or matrix, i.e., in so-called self-bound form. Alternatively, the molecular sieve may be composited with another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 percent by weight and more usually, particularly, when the composite is prepared in the form of beads, in the range of about 2 to about 80 weight percent of the composite.

The alkylation step may be carried out batchwise or on a continuous basis. Moreover, the reaction may be carried out in a fixed or moving bed reactor. Fixed bed operation is, however, preferred, typically with the alkylation reaction zone comprising one or a plurality of series-connected beds of alkylation catalysts.

The alkylation step is generally operated so as to achieve substantially complete conversion of the $C_3$ alkylating agent (isopropanol plus any added propylene) and hence the effluent from the alkylation reactor is composed mainly of cumene, coproduced water, unreacted benzene, and other reaction products. Hydrogen will also be present in the effluent if it is present in the feed. Water and, if present, hydrogen, are initially removed from the effluent and an aliquot of the resultant dried effluent stream is then separated and recycled to the alkylation zone in order to control the reaction temperature and to control the water content in the alkylation reactor.

If hydrogen is present in the effluent, hydrogen removal is typically achieved by passing the effluent directly from the alkylation reactor into a vapor/liquid separator to divide the effluent into a hydrogen-rich vapor stream and a hydrogen-depleted liquid stream. The hydrogen-rich vapor stream can then be recycled to the alkylation reactor, generally after being compressed and cooled to separate any entrained water and aromatics. The hydrogen-depleted liquid stream is subsequently separated into a water-rich aqueous stream and a water-depleted aromatic stream comprising cumene, unreacted benzene, and other reaction products. If hydrogen is not present in the effluent, the effluent stream from the alkylation reactor can be cooled, separated into a water-rich aqueous stream and a water-depleted aromatic stream comprising cumene, unreacted benzene, and other reaction products.

After separation and recycle of an aliquot of the dried effluent stream, the remainder of the dried effluent stream is passed to a distillation column, where the cumene is recovered and a benzene recycle stream containing unreacted benzene is separated for recycle back to the alkylation reaction zone.

Cumene Oxidation

The cumene recovered from the alkylation reaction effluent is converted to cumene hydroperoxide by a liquid phase oxidation process which is preferably carried out in a plurality of reactors connected in series. The oxidation process is conducted in the presence of an oxygen-containing gas, generally air, at a temperature from 50 to 120° C. and a pressure of 0 to 1 MPaG (gauge pressure). The total residence time in the oxidation reactors is usually from 3 to 20 hours.

The oxidation reaction may be carried out with or without a catalyst. Where a catalyst is employed, suitable catalysts include basic materials, such as carbonate and hydroxide compounds of alkali metals, such as lithium, sodium and potassium, and alkaline earth metals such as calcium and magnesium. These compounds may be used in solid form or in aqueous solution. The amount of catalyst (metal basis) is usually not more than 10 g equivalent, preferably 0.1 to 6 g equivalent per 1 ton of cumene.

The product of the oxidation reaction comprises a gas phase composed of spent air containing entrained cumene and a liquid phase which generally comprises 20 to 50% by weight of cumene hydroperoxide and 50 to 80% by weight of unreacted cumene, together with various by-products mainly composed of dimethyl phenyl carbinol (DMPC).

The gas phase product from the oxidation stage is cooled and then passed through a series of adsorbent beds, normally comprising charcoal, where the entrained cumene is removed before the spent air is vented to atmosphere or flared. The cumene collected by the charcoal adsorbers is recovered by desorption with low-pressure steam followed by condensation of the steam and decanting of the organic and water phases. The organic phase is then fed to a cumene recycle system described in more detail below.

The liquid phase product from the oxidation stage is heated in one or more stages, typically under vacuum, to remove most of the unreacted cumene and concentrate the cumene hydroperoxide in the product to 75 to 85 wt % before the product is fed to the cleavage step. The cumene vapor removed from the liquid phase product is cooled and combined with other cumene recycle streams produced in the process, such as the cumene recovered from the spent air, before being sent to the cumene recycle system.

Cumene Hydroperoxide Cleavage

The concentrated cumene hydroperoxide from the oxidation stage is decomposed or cleaved in a backmixed reactor in the presence of an acid catalyst, normally sulfuric acid, mainly to phenol and acetone, while most of the DMPC by-product is converted to α-methylstyrene (AMS). The cleavage reaction is typically carried out at a temperature of about 40° C. to about 60° C. and a pressure of about 0 kPa to about 500 kPa.

The acid catalyst added to the cleavage reactor must be neutralized to prevent yield loss due to side reactions and to protect against corrosion in the downstream fractionation section. This is typically achieved by injecting caustic into the cleavage reactor effluent before the effluent passes to the fractionation section.

After neutralization, the cleavage effluent is initially passed to an acetone recovery section comprising at least a crude acetone recovery column and a finished acetone recovery column. In the crude acetone recovery column, the effluent is separated into a crude phenol bottoms stream, which is fed to a phenol recovery section, and a crude acetone overhead stream. The overhead stream is then fed to the finished acetone recovery column, where unreacted cumene and water are removed as a bottoms stream and acetone product is recovered as an overhead stream. After removal of the water, the unreacted cumene is sent to the cumene recycle system.

The crude phenol stream removed in the acetone recovery section is fed to a phenol recovery section which again comprises a multi-column distillation section, where a mixed cumene/AMS stream is removed before the crude phenol undergoes various chemical treatments and fractionation to produce a finished phenol product.

The mixed cumene/AMS stream removed in the phenol recovery section is initially subjected to a caustic wash to remove any residual acid and is then passed to a hydrogenation reactor where the AMS undergoes mild hydrogenation in the presence of a platinum catalyst to produce cumene with high selectivity. The resultant cumene enriched product is then sent to the cumene recycle system.

Generally, the phenol and acetone recovered from the cleavage reaction effluent are used in a molar ratio of 2:1 to produce Bisphenol A, thereby resulting in a net surplus of acetone.

Acetone Hydrogenation

In the present process, the excess acetone from the cleavage stage is hydrogenated to produce isopropanol for recycle to alkylation stage. The acetone hydrogenation is effected by contacting the excess acetone with hydrogen in the presence of metal-containing catalyst. Generally the catalyst is Raney nickel, but other useful catalysts include nickel, copper-chromium, Raney nickel-copper, copper-zinc and platinum group metals, for example, platinum, palladium, ruthenium, rhodium, and similar metals on active carbon, aluminum and other carriers. The reaction temperature may range from 20° C. to about 350° C., but more generally is between about 40° C. and 250° C., such as between about 60° C. and 200° C. The hydrogenation may be carried out by either liquid, gas, or mixed gas-liquid phase reaction. The pressure may range from 100 kPa to 20,000 kPa, such as from about 500 to about 10,000 kPa. The hydrogen gas is generally present in a molar ratio relative to the acetone reactant of from 0.1:1 to 100:1, such as from 1:1 to 10:1.

The hydrogenation may be carried out in the presence or absence of a reaction medium. Examples of suitable media include alcohols such as methanol, ethanol, propanols and butanols. Also useful are glycols such as ethylene glycol, propylene glycol, diethylene glycol, and triethylene glycol; and ethers such as diisopropyl ether, dibutyl ether, ethylene glycol dimethyl ether, diglyme (diethylene glycol dimethyl ether) and triglyme. Aprotic polar solvents may also be used, for example, dimethylformamide, dimethylacetamide, acetonitrile, and dimethyl sulfoxide. Also useful are saturated hydrocarbons such as hexane, heptane, cyclopentane, and cyclohexane. Water can also be used as a solvent in the hydrogenation reaction.

The hydrogenation step may be carried out batchwise or on a continuous basis. Depending on the shape of a particular catalyst used, the reaction may be carried out in a fluidized bed using powder catalyst or a fixed bed using granular catalyst. Fixed bed operation is preferred in view of ease of separation of the catalyst from the reaction mixture and simplicity of the reaction system.

The hydrogenation reaction is exothermic and, to avoid excessive temperature rise, part of the reaction effluent, composed mainly of isopropanol, can be cooled and recycled to hydrogenation reactor inlet. In one embodiment, the weight ratio of liquid recycle to acetone feed is between about 1:1 and about 100:1.

In addition, part of the unreacted hydrogen in the hydrogenation reaction effluent can be recycled to the hydrogenation reactor inlet so as to reduce the level of hydrogen in the isopropanol-containing feed to the alkylation step.

Treatment of Isopropanol Recycle Stream

In practice, the isopropanol produced in the process described above will contain relatively high levels (up to 10 ppm by weight) of nitrogen compounds generated as a result of the use of amines as neutralizing agents and corrosion inhibitors in the oxidation and cleavage stages of the process. If not removed or reduced in concentration before the isopropanol is recycled to the alkylation stage, these nitrogen compounds will act as poisons to the molecular sieve alkylation catalyst and thereby reduce cycle life of the catalyst.

In a first embodiment, the cycle life of the alkylation catalyst is enhanced by removing nitrogen-containing impurities from the aliquot of the dried alkylation effluent stream before this aliquot is recycled to the alkylation reactor. In this embodiment, therefore, the nitrogen-containing impurities are not directly removed from the recycled isopropanol but the concentration of these impurities in the total feed (isopropanol plus recycled benzene) to the alkylation reactor is reduced, typically to less than 0.2 ppm by weight.

In a modification of the first embodiment, in which the $C_3$ alkylating agent comprises recycled isopropanol, some or all of the isopropanol feed may be mixed with the aliquot of the dried effluent stream before the resultant combined stream is treated to remove nitrogen-containing impurities. Similarly, some or all of the fresh benzene feed, and some or all of the recycle benzene from product recovery section, can be added to the aliquot of the dried effluent stream before purification. In this way, some removal of nitrogen impurities from the isopropanol and/or the fresh benzene can also be accomplished.

In a second embodiment, improvement in the alkylation catalyst life is achieved by combining the recycled isopropanol with fresh benzene and then treating this combined stream to remove nitrogen-containing impurities both in the recycled isopropanol and the benzene feed. The combined stream is then fed to the alkylation reactor. If desired, the dried recycle stream may be included in the combined stream before the stream is treated to remove nitrogenous impurities.

In each of the above embodiments, treatment to remove nitrogen-containing impurities is generally carried out by (a) passing the relevant stream through one or more vessels containing at least one solid adsorbent, such as a molecular sieve, a resin, an acidic clay or a membrane, and/or (b) washing the stream with an acidic aqueous solution, such as dilute sulfuric acid. In this way the nitrogen content of the total feed to the alkylation reaction can be reduced to less than 0.2 ppm by weight. In one embodiment, the at least one solid adsorbent comprises a clay. Suitable clays include bentonite or other montmorillonite-containing clays. In some embodiments, the clay may have been activated by treatment with an acid, such as sulfuric acid. The clay is typically used as a granular or powder material. A suitable example of a clay adsorbent for use in the present process is the F-24 series clay supplied by BASF.

The invention will now be more particularly described with reference to the following non-limiting Examples and the accompanying drawings.

Example 1

Alkylation with Purchased Isopropanol

Figure 1:
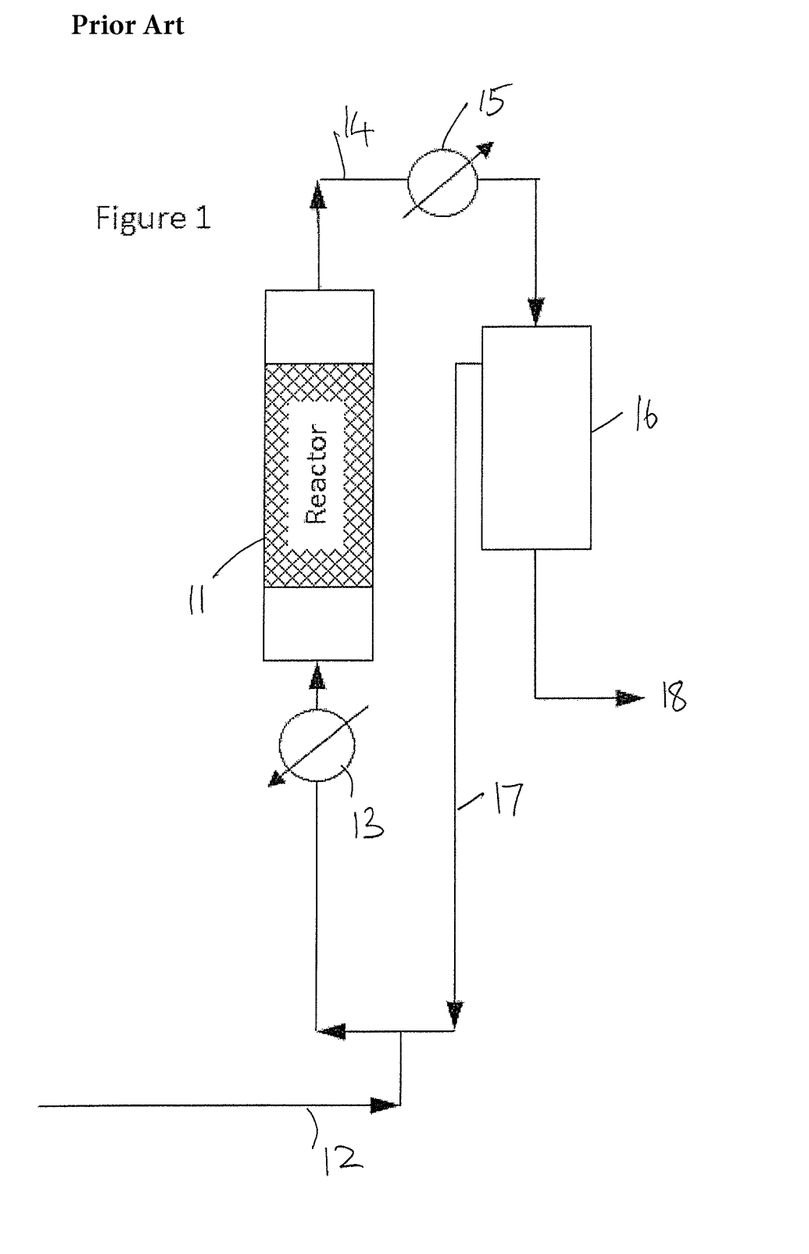
FIG. 1 is a schematic diagram of a known process for producing cumene by alkylating benzene with isopropanol.

Referring to FIG. 1, an alkylation test of benzene with purchased isopropanol was carried out in a fixed bed reactor 11, made from a ¾ inch (19 mm) diameter Schedule 40 Stainless Steel 316 pipe with a total length of 34 inches (864 mm). A multi-point thermocouple probe (not shown) was placed along the center axis of the reactor 11 so that the temperature at various points in the reactor could be monitored. A positive displacement pump (not shown) was used to supply a mixture of benzene and isopropanol from a storage tank by way of line 12 to a heat exchanger 13 and then to the reactor 11. The flow rates of the benzene/isopropanol mixture were set by pump settings and monitored by electronic weight scales. The reactor operating conditions were controlled and monitored by an automatic control system. The effluent from the reactor 11 was fed by line 14 to a cooler 15, where the effluent was cooled to near ambient temperature before being fed to a decanter 16. Free water was removed from the effluent in the decanter 16 and a portion of the dewatered reactor effluent was circulated through line 17 back to the reactor 11 by a centrifugal pump to control the temperature rise and the moisture content in the reactor 11. The remainder of the dewatered reactor effluent was removed from the decanter 16 via line 18 for recovery of the cumene.

The feedstock and reactor effluent were analyzed by two Hewlett Packard 5890 Series II Gas Chromatographs, one equipped with a Chrompack CP-Wax 52CB column having an inside diameter of 0.25 mm, film thickness of 0.5 µm, and length of 60 meters, and the other one equipped with an Agilent DB-1 column having an inside diameter of 0.25 mm, film thickness of 0.5 µm, and length of 100 meters.

In the test, 60 grams of an MCM-22 family catalyst was loaded into the fixed bed reactor and dried with benzene at 150° C. for four days. A feed comprised of 79.6 wt % benzene and 20.4 wt % isopropanol purchased from Sigma-Aldrich, equivalent to a benzene to isopropanol molar ratio of 3:1, was fed to the reactor at 150 grams per hour, giving an isopropanol WHSV of 0.5 hr$^{-1}$. No nitrogen compounds were detected in this purchased isopropanol. The reactor circulation was adjusted to give a moisture content of about 1.0 wt % in the reactor effluent. The inlet temperature was 210° C., the reactor pressure was maintained at about 4,700 kPa, and the reaction took place in liquid phase. Because the isopropanol conversion remained 100% throughout this example, the catalyst stability was also monitored by percent temperature rise at 22% catalyst loading (PTR$_{22}$) which is defined below:

$$PTR_{22}=[T_{22}-T_{inlet}]/[T_{outlet}-T_{inlet}]\times 100\%$$

where $T_{inlet}$ and $T_{outlet}$ are the reactor temperature measured at the inlet and the outlet of the catalyst bed, respectively, and $T_{22}$ is the temperature measured at 22% of the length from the inlet of the catalyst bed. Because the isopropanol alkylation is an exothermic reaction, the temperature of the reaction mixture goes up in the reactor as the conversion increases and reaches the final temperature when the reaction is completed. The percentage temperature rise PTR$_{22}$ measured at the first 22% of the catalyst loading gives an indication of the conversion in the first 22% of the catalyst bed. When the catalyst is stable, the conversion in the first 22% of the catalyst bed is stable and $PTR_{22}$ remains essentially constant. When the catalyst deactivates, the conversion in the first 22% of the catalyst bed goes down gradually (while the remainder of the catalyst bed continues to bring the reaction to completion) and the $PTR_{22}$ goes down. A stable $PTR_{22}$ therefore indicates that the catalyst bed is stable while a decreasing $PTR_{22}$ indicates that the catalyst bed is deactivating.

For 68 days with Sigma-Aldrich isopropanol feed, the $PTR_{22}$ was very stable with a nearly immeasurable average decline rate of less than 0.05% per day. The isopropanol conversion remained 100% for the same period of time. These indicate that the MCM-22 family catalyst tested had very high activity and was very stable with the purchased Sigma-Aldrich isopropanol feed.

Example 2

Hydrogenation of Acetone to Isopropanol

A batch of acetone obtained from a commercial phenol/acetone plant was hydrogenated to isopropanol by contacting the acetone feed with hydrogen in the presence of a nickel hydrogenation catalyst at a temperature of about 80° C. and a pressure of about 3,600 kPa. A portion of the reactor effluent was recycled back to the reactor inlet to keep the temperature rise below about 30° C. The acetone conversion was about 99%. The isopropanol product was analyzed by a gas chromatograph equipped with a Nitrogen-Phosphorous Detector (NPD) and found to contain about 0.2 wtppm nitrogen.

Example 3

Alkylation with Isopropanol Produced from Acetone Using Guard Bed

Figure 2:
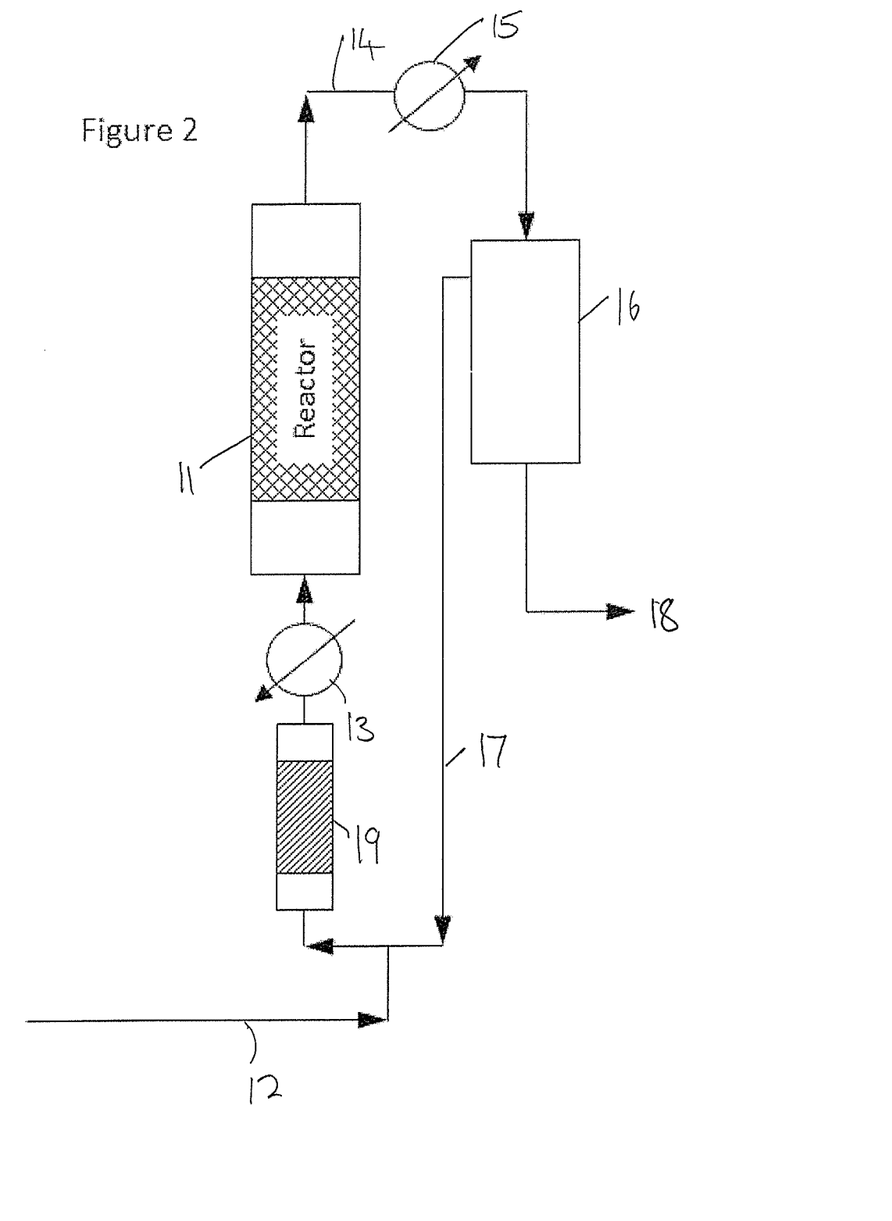
FIG. 2 is a schematic diagram of a process for producing cumene by alkylating benzene with isopropanol according to a first example of the invention.

The same reactor setup and catalyst loading described in Example 1 were used in this Example and, in addition, a guard bed 19 loaded with 30 grams of fresh BASF F-24 clay was installed to treat the total reactor feed comprising dried effluent recycle stream and combined benzene/isopropanol feed. A schematic diagram of the reactor system including the guard bed 18 is shown in FIG. 2. The guard bed 19 put into service after 86 days on-stream while the other operating conditions were kept the same as those in Example 1. The catalyst was very stable with the guard bed 19 and another batch of purchased isopropanol feed, showing no measurable $PTR_{22}$ decline rate.

After 94 days on-stream, a feed comprised of 79.6 wt % benzene and 20.4 wt % of the isopropanol produced in Example 2 was introduced into the reactor 11 in place of the mixture of benzene and purchased isopropanol. A measurable and continuous decline of $PTR_{22}$ started immediately. The feed comprised of 79.6 wt % benzene and 20.4 wt % of the isopropanol produced in Example 2 continued for 100 days while the guard bed 19 remained in service the whole time and the other operating conditions were kept the same as those in Example 1. The average $PTR_{22}$ decline rate for these 100 days was about 0.5% per day. The isopropanol conversion during this same period of time remained at 100%.

Example 4

Alkylation with Isopropanol Produced from Acetone Using Guard Bed

Figure 3:
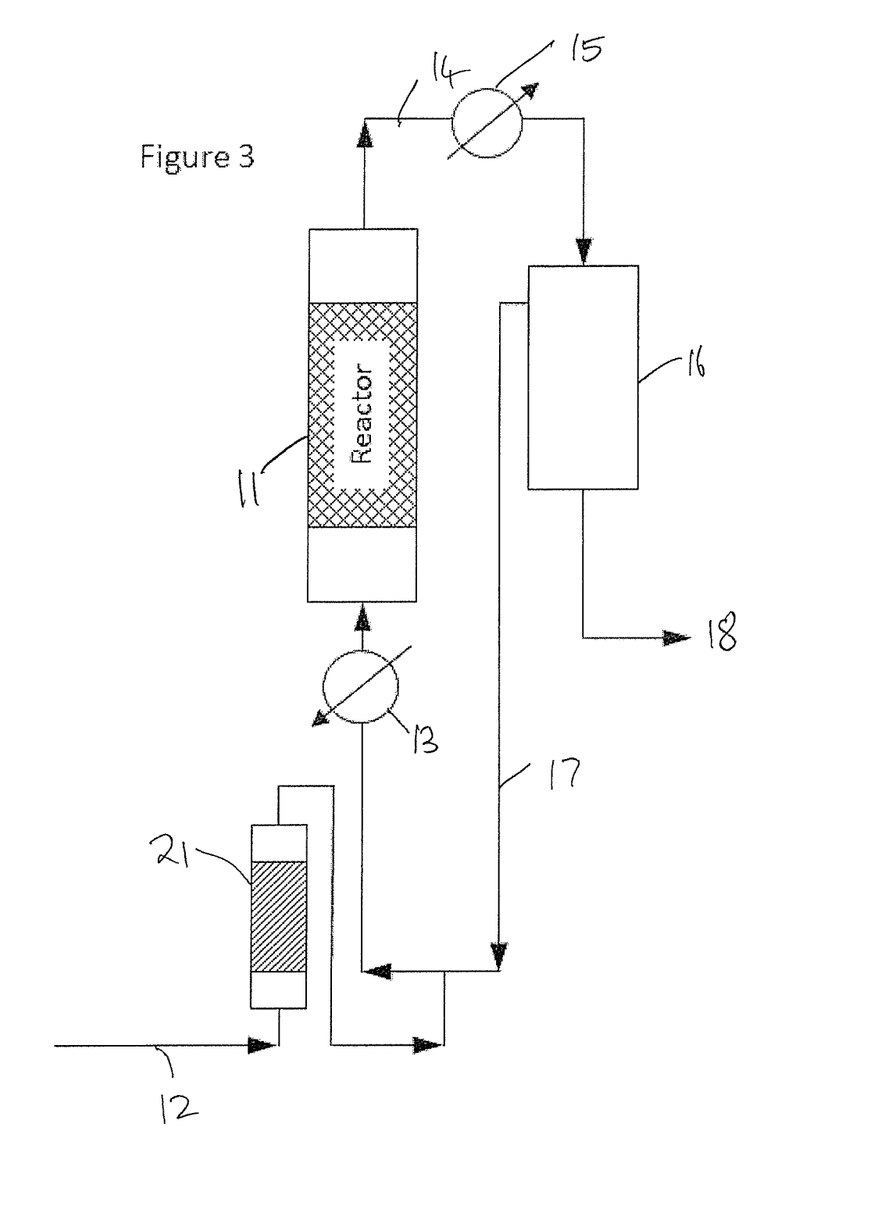
FIG. 3 is a schematic diagram of a process for producing cumene by alkylating benzene with isopropanol according to a second example of the invention.

The same reactor setup and catalyst loading described in Example 3 were used in this Example, except a guard bed 21 loaded with 6 grams of fresh BASF F-24 clay was installed to treat the combined benzene/isopropanol feed, but not the dried effluent recycle stream. A schematic diagram of the reactor system including the guard bed 21 is shown in FIG. 3. The guard bed 21 was and put into service after 194 days on-stream. Guard bed 19 was by-passed 3 hours after guard bed 21 was placed on-stream. Feed comprised of 79.6 wt % benzene and 20.4 wt % of the isopropanol produced in Example 2 continued to be fed to the reactor 11 for another 21 days while the guard bed 21 remained in service and guard bed 19 was by-passed the whole time. The other operating conditions were kept the same as those in Example 1. The average $PTR_{22}$ decline rate was about 0.7% per day for these 21 days.

The guard bed 21 was replaced with a larger guard bed containing 12 grams of fresh BASF F-24 after 215 days on-stream. Feed comprised of 79.6 wt % benzene and 20.4 wt % of the isopropanol produced in Example 2 continued to be fed to the reactor 11 for another 22 days while the new guard bed 21 remained in service and guard bed 19 was by-passed the whole time. The other operating conditions were kept the same as those in Example 1. The average $PTR_{22}$ decline rate remained the same as before at about 0.7% per day for these 22 days. The isopropanol conversion on 194 and 237 days on-stream were 100% and 99.9986%, respectively. The average isopropanol conversion decline rate in this 43-day period when guard bed 21 was in service was therefore about 0.00003% per day.

Example 5

Alkylation with Isopropanol Produced from Acetone Without Guard Bed

The same reactor setup and catalyst loading described in Examples 3 and 4 were used in this example. The guard beds 19 and 21 were both by-passed after 237 days on-stream. Feed comprised of 79.6 wt % benzene and 20.4 wt % of the isopropanol produced in Example 2 continued to be fed to the reactor 11 for another 11 days while both guard beds 19 and 21 were by-passed. The other operating conditions were kept the same as those in Example 1. The average $PTR_{22}$ decline rate was about 2.2% per day for theses 11 days. The isopropanol conversion during this period decreased from 99.9986% on 237 days on-stream to 99.9963% on 248 days on-stream. The average isopropanol conversion decline rate was therefore 0.00021% per day.

The average $PTR_{22}$ and isopropanol conversion decline rates observed in Examples 3-5 are listed in Table 1. It is noted that the average decline rates of both $PTR_{22}$ and isopropanol conversion without any guard bed (Example 5) are much higher than those observed with the guard bed 19 (Example 3) and with the guard bed 21 (Example 4).

The above examples clearly demonstrate that the catalyst deactivation rate can be greatly reduced by removing the nitrogenous species contained in the isopropanol feed produced from acetone.

TABLE 1

Average Decline Rates with Produced Isopropanol

|  | With guard bed 19 | With guard bed 21 | No guard bed |
|---|---|---|---|
| Run length | 100 days | 43 days | 11 days |
| Average $PTR_{22}$ decline | 0.5% | 0.7% | 2.2% |

TABLE 1-continued

Average Decline Rates with Produced Isopropanol

| | With guard bed 19 | With guard bed 21 | No guard bed |
|---|---|---|---|
| rate | per day | per day | per day |
| Average isopropanol conversion decline rate | None detected | 0.00003% per day | 0.00021% per day |

The invention claimed is:

1. A process for producing cumene, the process comprising:
    (a) contacting benzene with a $C_3$ alkylating agent comprising isopropanol, and optionally propylene, under alkylation conditions such that at least part of said $C_3$ alkylating agent reacts with the benzene to produce an alkylation effluent comprising cumene, unreacted benzene and water;
    (b) recovering cumene from said alkylation effluent;
    (c) removing water from said alkylation effluent to form a dried effluent stream;
    (d) treating an aliquot of the dried effluent stream to remove nitrogenous impurities therefrom and produce a purified recycle stream; and
    (e) recycling at least part of the purified recycle stream to said contacting (a).

2. The process of claim 1, wherein the contacting (a) takes place in the presence of a molecular sieve alkylation catalyst.

3. The process of claim 2, wherein said alkylation catalyst comprises at least one zeolite catalyst selected from the group consisting of ZSM-3, ZSM-4, ZSM-5, ZSM-11, ZSM-12, ZSM-14, ZSM-18, ZSM-20, ZSM-22, ZSM-23, ZSM-35, ZSM-48, zeolite beta, zeolite Y, Ultrastable Y (USY), Deluminized Y (Deal Y), mordenite, MCM-22, PSH-3, SSZ-25, ERB-1, ITQ-1, ITQ-2, MCM-36, MCM-49, MCM-56, and UZM-8.

4. The process of claim 1, wherein the alkylation conditions comprise a temperature of 20° C. to 350° C., a pressure of 100 kPa to 20,000 kPa, and a molar ratio of benzene to $C_3$ alkylating agent (isopropanol plus any propylene) fed to said alkylation zone of 0.1:1 to 100:1.

5. The process of claim 1, wherein the $C_3$ alkylating agent comprises a mixture of isopropanol and propylene at a molar ratio of isopropanol to propylene of about 100 to 1 to about 1 to 100.

6. The process of claim 1, wherein fresh benzene, recycle benzene and/or fresh $C_3$ alkylating agent is mixed with the aliquot of the dried recycle stream prior to said treating (c).

7. The process of claim 1, wherein the treating (d) includes passing the aliquot of the dried recycle stream through at least one solid adsorbent.

8. The process of claim 7, wherein the at least one solid adsorbent is selected from a molecular sieve, a resin, an acidic clay and a membrane.

9. The process of claim 1, wherein the treating (d) includes washing the aliquot of the dried recycle stream with an acidic water solution.

10. The process of claim 1, wherein cumene is recovered in (b) from the portion of the dried effluent stream remaining after separation of the aliquot for the treating (d).

11. An integrated process for producing phenol comprising the process of producing cumene as claimed in claim 1 and the following additional steps:
    (f) oxidizing at least part of the cumene recovered in (b) to form cumene hydroperoxide;
    (g) cleaving at least part of the cumene hydroperoxide from (f) to form a cleavage product stream containing phenol and acetone;
    (h) separating at least part of the acetone from the cleavage product stream;
    (i) hydrogenating at least part of the acetone separated in (h) to produce isopropanol; and
    (j) recycling at least part of the isopropanol produced in (i) to the contacting (a).

12. A process for producing cumene comprising, the process comprising:
    (a) mixing fresh and/or recycled benzene with a $C_3$ alkylating agent comprising isopropanol, and optionally propylene, to produce a combined feed stream;
    (b) treating at least part of said combined feed stream to remove nitrogenous impurities therefrom and produce a purified combined feed stream; and
    (c) contacting said purified combined feed stream with an alkylation catalyst in an alkylation zone under alkylation conditions such that at least part of said isopropanol and benzene react to produce an alkylation effluent comprising cumene.

13. The process of claim 12, wherein said treating (b) includes passing at least part of said combined feed stream through at least one solid adsorbent.

14. The process of claim 13, wherein the at least one solid adsorbent is selected from a molecular sieve, a resin, an acidic clay and a membrane.

15. The process of claim 12, wherein the treating (b) includes washing at least part of the combined feed stream with an acidic water solution.

16. The process of claim 12, wherein the alkylation effluent also comprises water and unreacted benzene and the process further comprises:
    (i) removing water from at least part of the alkylation effluent to form a dried effluent stream; and
    (ii) including said dried effluent stream in said combined feed stream produced in (a).

17. An integrated process for producing phenol comprising the process of producing cumene as claimed in claim 12 and the following additional steps:
    (d) oxidizing at least part of the cumene produced in (c) to form cumene hydroperoxide;
    (e) cleaving at least part of the cumene hydroperoxide from (d) to form a cleavage product stream containing phenol and acetone;
    (f) separating at least part of the acetone from the cleavage product stream;
    (g) hydrogenating at least part of the acetone separated in (f) to produce isopropanol; and
    (h) recycling at least part of the isopropanol produced in (g) to the mixing (a).

* * * * *